United States Patent
Christiansen et al.

(10) Patent No.: US 7,755,051 B2
(45) Date of Patent: Jul. 13, 2010

(54) METHOD AND DEVICE FOR THE QUANTITATIVE ANALYSIS OF SOLUTIONS AND DISPERSIONS BY MEANS OF NEAR INFRARED SPECTROSCOPY

(75) Inventors: Christian-Peter Christiansen, Frankfurt (DE); Hans-Joachim Ploss, Kriftel (DE); Richard Mertens, Laupheim (DE); Heino Prinz, Laupheim (DE)

(73) Assignees: Sanofi-Aventis Deutschland GmbH, Frankfurt am Main (DE); Uhlmann Visiotec GmbH, Laupheim (DE)

( * ) Notice: Subject to any disclaimer, the term of this patent is extended or adjusted under 35 U.S.C. 154(b) by 0 days.

(21) Appl. No.: 11/762,968

(22) Filed: Jun. 14, 2007

(65) Prior Publication Data

US 2008/0230700 A1    Sep. 25, 2008

Related U.S. Application Data

(63) Continuation of application No. 11/470,370, filed on Sep. 6, 2006, now abandoned, which is a continuation of application No. 11/302,870, filed on Dec. 14, 2005, now abandoned, which is a continuation of application No. 10/861,675, filed on Jun. 4, 2004, now abandoned.

(60) Provisional application No. 60/511,207, filed on Oct. 15, 2003.

(30) Foreign Application Priority Data

Jun. 6, 2003   (DE) ................................... 10326152

(51) Int. Cl.
   *G01N 21/35* (2006.01)

(52) U.S. Cl. .............................. 250/339.12; 250/339.11

(58) Field of Classification Search ............. 250/339.12
   See application file for complete search history.

(56) References Cited

U.S. PATENT DOCUMENTS 5,227,856 A   7/1993   Reed et al.

(Continued)

FOREIGN PATENT DOCUMENTS

EP   0887638   12/1998

(Continued)

OTHER PUBLICATIONS

Blanco,M. et al., Identification and Quantitation Assays for Intact Tablets of Two Related Pharmaceuticval Preparation by Reflectance Near-Infrared Spectroscopy: Validation of the Procedure, Journal of Pharmaceutical and Biomedical Analysis vol. 22 (2000) pp. 139-148.

(Continued)

*Primary Examiner*—David P Porta
*Assistant Examiner*—Marcus H Taningco

(57) ABSTRACT

The present invention relates to a method for quantifying the composition of a product, including: irradiating the product with a radiation source in the near infrared range; receiving radiation which is reflected by or transmitted through the product; providing an output signal corresponding to the intensity of the radiation received at a number of different wavelengths; and determining whether or not the product lies within predetermined integrity criteria on the basis of the output signal using a mathematical method. The moving product contains a solution or homogeneous dispersion and the content of at least one substance contained in the dispersion or solution is quantitatively determined on the basis of the output signal. The invention also relates to a device for carrying out this method.

8 Claims, 6 Drawing Sheets

U.S. PATENT DOCUMENTS

| | | | |
|---|---|---|---|
| 5,305,887 A | 4/1994 | Krieg et al. | |
| 5,361,912 A | 11/1994 | Krieg et al. | |
| 5,405,014 A * | 4/1995 | Krieg et al. | 209/524 |
| 5,614,718 A | 3/1997 | Brace et al. | |
| 5,818,045 A | 10/1998 | Mark et al. | |
| 5,900,634 A | 5/1999 | Soloman et al. | |
| 5,945,676 A | 8/1999 | Khalil et al. | |
| 6,040,578 A | 3/2000 | Malin et al. | |
| 6,707,556 B2 | 3/2004 | Turner et al. | |
| 6,845,326 B1 | 1/2005 | Panigrahi et al. | |
| 2001/0050339 A1* | 12/2001 | Panigrahi et al. | 250/339.07 |
| 2002/0109094 A1 | 8/2002 | Goetz et al. | |
| 2004/0046122 A1 | 3/2004 | Klaas et al. | |
| 2004/0084623 A1 | 5/2004 | Long et al. | |
| 2004/0255649 A1 | 12/2004 | Zougari et al. | |

FOREIGN PATENT DOCUMENTS

| | | |
|---|---|---|
| GB | 2297377 | 7/1996 |
| GB | 2297377 A * | 7/1996 |
| WO | WO 01/16578 | 3/2001 |
| WO | WO 02/065072 | 8/2002 |

OTHER PUBLICATIONS

MacDonald, B.F. et al., Some Applications of Near-Infrared Reflectance Analysis in the Pharmaceutical Industry, Journal of Pharmaceutical and Biomedical Analysis vol. 11, No. 11/12 (1993) pp. 1077-1085.

* cited by examiner

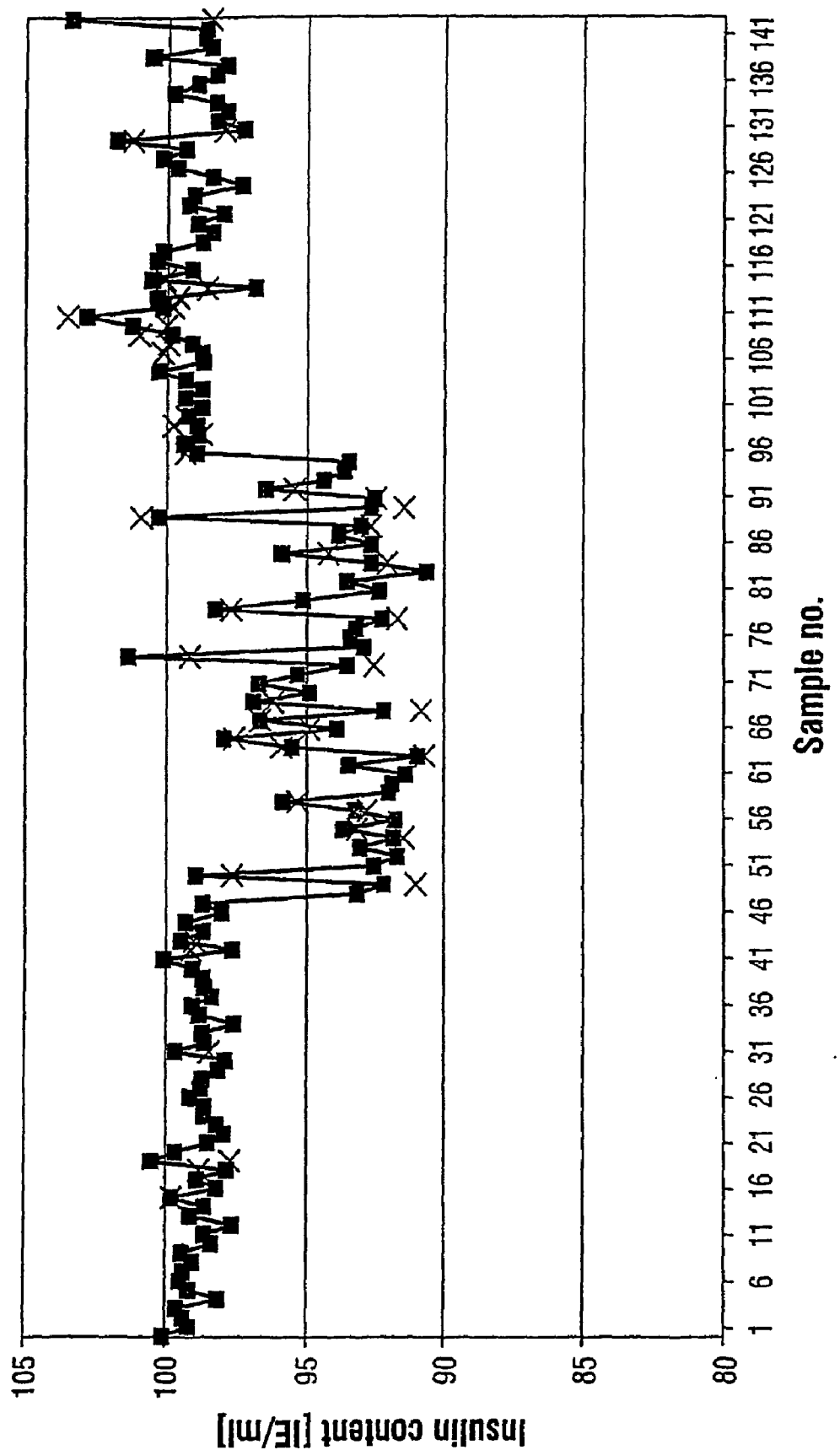

METHOD AND DEVICE FOR THE QUANTITATIVE ANALYSIS OF SOLUTIONS AND DISPERSIONS BY MEANS OF NEAR INFRARED SPECTROSCOPY

The invention relates to a method and a device for the quantitative analysis of solutions and dispersions, such as solutions and dispersions for pharmaceutical purposes, by means of near infrared spectroscopy.

In the field of medicament production, efforts are constantly being made to improve the quality control of medicament safety. Production is in this case carried out according to the international standard of good (current) manufacturing practice (cGMP), and which is stipulated by the pharmaceutical monitoring authorities (for example the US American Food and Drug Administration, FDA). Authorization to produce medicaments may be withdrawn from a company in the event of serious infringements against this manufacturing practice.

Physicochemical and microbiological testing and approval of a product is an important part of good manufacturing practice. In the course of this testing, a plurality of parameters describing the quality of the product are tested and compared against specifications. The specifications are found either in the licensing documents or in the international pharmacopeas. The product can be marketed as long as all the specifications are complied with. One of these test parameters is the active agent content, which needs to be quantitatively determined. The quantitative determination is usually carried out by spot checks and in the form of destructive testing. Liquid chromatographic or gas chromatographic methods, or spectroscopy methods, which require sample preparation, are preferably used as the analysis methods. These methods are distinguished by relatively high precision, although the analysis speed is very slow. These methods are therefore unsuitable for providing a result inline, that is to say directly during the manufacturing process. Furthermore, the measurement cannot be carried out on products in primary packaging.

The disadvantage of spot-check batch testing is that trends or anomalous events cannot be identified during production, for example when filling suspensions. There is a risk that products will be approved as compliant with specification even though they do not actually lie within the approval limits. These "out of specification" (OOS) products may, for example, occur owing to temporary production problems or product admixtures.

The requirements for complete, rather than spot-check, testing of each produced unit on the running production line can be satisfied only by nondestructively operating and sufficiently fast analysis methods. Both requirements can in principle be satisfied by spectroscopy methods. The majority of spectroscopy methods, however, are unsuitable for providing quantitative analysis results without prior sample preparation, for example by dissolving, concentrating or diluting the samples. As a rule, these methods are also unsuitable for producing quantitatively evaluable spectra through the primary packaging (for example glass or plastic) and/or from dispersive systems. Only the relatively narrow wavelength range of near infrared radiation (NIR), which extends from 800 to 2500 nm, can be used to perform such tasks.

Methods in which objects conveyed on a belt are controlled, that is to say in real time and essentially fully, are known in connection with refuse sorting and the sorting of plastic parts. Some of these methods use near infrared (NIR) spectroscopy.

EP-B 1 030 740 discloses a method for identifying and sorting objects conveyed on a belt, especially for refuse sorting, in which the material composition of the objects is spectroscopically recorded by means of an NIR measuring instrument, and the sorting is carried out as a function of the spectroscopy result by removing objects from the conveyor belt.

EP-B 0 696 236 discloses a method for sorting plastic parts, in which the plastic parts are transported past a material detection system, which determines the substance class of each material part by contactless sampling thereof in a measurement field. The material detection system contains a contactlessly operating material sensor, for example a microwave sensor, an x-ray sensor or a spectroscopy sensor operating in the near infrared range.

In the filling of suspensions for pharmaceutical purposes, fluctuations may occur during filling owing to segregation processes. These fluctuations can cause some of the filled units (for example cartridges) to have content values for the active substance (for example insulin) or auxiliaries (for example protamine sulfate) which lie outside the requisite specification (for example from 95.0 to 105.0% of the nominal value for insulin).

European Patent Application EP-A 0 887 638 describes a method and a device for analyzing the composition of a moving sample, with a near infrared (NIR) radiation source being used and the NIR light reflected by the sample being detected. Tablets or capsules on a conveyor belt are analyzed as the samples.

In principle, high pressure (performance) liquid chromatography (HPLC) is suitable for the quantitative analysis of liquid samples. However, quality control by quantitative analysis of samples by means of HPLC has the disadvantage that it is slow and does not take place nondestructively. It is therefore only suitable for spot-check quality control. This method is quite unsuitable for line control, in which each of the filled product units needs to be checked for whether its active agent content lies within the requisite specifications.

Herkert (2001, Dissertation, Eberhard-Karls University, Tubingen) has evaluated an NIR method for line control of pharmaceuticals on a packaging line. The purpose of the work was, in particular, to evaluate the VisioNIR® spectrometer (Uhlmann Visio Tec GmbH, Laupheim). The evaluation was carried out, inter alia, on insulin suspensions.

Herkert detected the re-emission in his work, that is to say the diffuse reflection of the incident NIR light. Only qualitative discrimination of three different insulin types was carried out in this case, which differed in their composition of soluble and crystalline insulin. The spectral differences in the raw spectra or derivative spectra were used to assess whether it is possible to identify the individual products with the aid of NIR spectra. Pattern recognition could be carried out on the basis of these differences with the aid of principal component analysis (PCA) or the VisioNIR® evaluation statistics. Quantitative analysis was not carried out. The measurement of liquids (insulin suspensions) was not possible with the VisioNIR® spectrometer instrumentation over the packaging line. Scattering effects from the glass and in the air space above the suspension prevented valid spectral recording (see the cited dissertation by Herkert, page 76, $2^{nd}$ paragraph).

It is an object of the invention to provide a method for the analysis of products which contain a solution or dispersion, for example for pharmaceutical purposes, with which rapid quantitative determination of substances contained in the solution or dispersion is possible, and which is noninvasive and operates nondestructively. In particular, the method should be suitable for the analysis of a large number of product units per unit time, for example in order to be used for line control of the composition of solutions or dispersions when they are being filled in a filling system or a packaging line during the production process. Line control is in this case intended to mean realtime control, which includes essentially all of the product units.

Surprisingly, it is now been found that it is possible to employ a method for quantifying the composition of a product, in particular a moving product, with the following steps:

irradiating the product with a radiation source in the near infrared range;

receiving radiation which is reflected by or transmitted through the product, and providing an output signal corresponding to the intensity of the radiation received at a number of different wavelengths;

determining whether or not the product lies within predetermined integrity criteria on the basis of the output signal using a mathematical method.

The method according to the invention is one wherein the moving product contains a solution or homogeneous dispersion, and the content of at least one substance contained in the dispersion or solution is quantitatively determined on the basis of the output signal.

In the context of the present invention, quantitatively means that the content of at least one substance to be determined in the solution or dispersion can be determined unequivocally and correctly within a range of in general ±3%, preferably ±5%, particularly preferably ±10% and in particular ±20% of the setpoint value (for example defined by the pharmaceutical formulation). Unequivocally means that the values determined by the method according to the invention are reliable with a relative standard deviation of no more than 1.5%, preferably no more than 1%, particularly preferably no more than 0.5%. Reference values which have been determined by means of a tried and tested reference method, for example a chromatographic method such as HPLC, are in this case regarded as correct, with the reference value and the value determined by the method according to the invention deviating from each other by at most 5%, preferably at most 3%, particularly preferably at most 1%.

The product may contain any solutions or dispersions, usually in a container which is transparent for NIR radiation. If the product contains a dispersions, this will in general be a liquid dispersion such as an emulsion or suspension. The substance contained in the dispersion, and whose content is intended to be quantitatively determined by the method according to the invention, may be present only in the continuous phase or only in the disperse phase, or alternatively distributed in both phases. The dispersions or solutions may be pharmaceutical products, which contain a dissolved and/or dispersed active agent. The substance whose content is intended to be quantitatively determined may, for example, be a pharmaceutical active agent or an auxiliary. For example, the solution may be an insulin solution or the dispersion may be an insulin suspension, which contains suspended crystalline or amorphous insulin optionally together with dissolved insulin, for example insulins of the NPH type (neutral protamine Hagedorn insulin preparations), mixtures of NPH insulins and dissolved insulins or insulin zinc suspensions. The insulins may, for example, be human insulin or its genetically or enzymatically modified analogs.

The solutions or dispersions may be present in primary packaging, for example cartridges, vials or bottles, for example made of glass or plastic. These may be located on a conveyor belt and studied by the method according to the invention during the delivery process, for example from a filling system to a packaging machine.

The method according to the invention may be carried out in a reflection arrangement or in a transmission arrangement.

In one embodiment of the method, operation is carried out in a transmission arrangement, that is to say the radiation transmitted through the product is received.

The product whose composition is intended to be verified is irradiated with a radiation source in the near infrared range. The near infrared range conventionally comprises the wavelength range of from 800 to 2500 nm. Suitable radiation sources are, for example, mercury halogen lamps.

The radiation reflected or transmitted by the product is received by a radiation reception device. An output signal corresponding to the intensity of the radiation received at a number of different wavelengths is obtained. This may be done by splitting the received radiation into a number of wavelengths in a spectrometer and detecting it with a photodiode array. The current from each photodiode may be integrated over a preselected time and subsequently converted into a digital signal by means of an analog/digital (A/D) converter.

The integration time may be started by a trigger, for example a photoelectric barrier, as a function of the position of the moving object.

The content of the at least one substance contained in the dispersion or solution is quantitatively determined using a mathematical method on the basis of the output signal obtained at the different wavelengths. Suitable mathematical methods are multivariate data analysis methods. Suitable methods are, for example, the PLS (partial least squares) method or principal component analysis (PCA). Such methods are known to the person skilled in the art.

The mathematical method may use weighting factors in order to reduce the effect of spurious variabilities, not attributable to the composition, in the recorded NIR spectra during evaluation, and to emphasize spectral features which do not vary between samples of the same product type.

Conventionally, calibration is carried out at least once by quantitatively determining the content of the at least one substance in the solution or dispersion by means of an alternative method.

A preferred alternative method which is used for the calibration is HPLC. The calibration may be repeated at regular intervals while the method according to the invention is being carried out.

In one embodiment of the method according to the invention, the mathematical method described on page 5, line 47 to page 8, line 12 of EP-B 0 887 638 is used. EP-B 0 887 638 is in this respect fully included in the present description. Weighting factors are used in the mathematical method described therein.

The data of the raw spectra, which reflect the radiation intensities in intervals (for example 3.8 nm) are in this case corrected, a standard value being obtained which is independent of the characteristics of the spectrometer and of the radiation reception device. The intensities calibrated in this way are smoothed in order to minimize effects due to signal noise, with a Gaussian smoothing function being used. The data may be autoscaled order to minimize the systematic effects. To this end, the individual intensities of the spectrum are normalized to a standard deviation of zero and variance of one over the entire wavelength range. The differences of the individual spectra with respect to slope and spectral features of the individual product samples may be emphasized by forming the $1^{st}$ derivative. Instead of the $1^{st}$ derivative, it is also possible to use the $2^{nd}$ or $0^{th}$ derivative.

The differences between a model spectrum and the spectrum of the product sample (sample spectrum) are then calculated for each measured wavelength. If the differences exceed a specified limit, then the sample is identified as being significantly different from the model.

The model (master model) is set up from the calibration data records of a number of equivalent samples of the different product types. An average spectrum is then calculated. If the variance of the model per measurement point (wavelength) is considered, then spectral ranges with significantly high standard deviations are found. These regions reflect the variability of calibration samples (equivalent in respect of their composition) with respect to various extraneous factors, for example differences in the glass or in the position of a cartridge. In order to minimize the effect of these spurious variances, weighting factors are calculated. These weighting factors weight spectral ranges with a smaller standard deviation more highly than ranges with a high standard deviation. The weighting factor is found from the standard deviation of the difference between the intensity values and the intensity value of the model at each wavelength.

The Euclidian distance of every data record within the calibration sample data records is subsequently calculated by using the weighting factors. The mean of this value corresponds to the standard deviation of the model. The mean Euclidian distance of the model is also calculated at the end of the modeling. This value is given as a reference quantity in terms of model standard deviations.

Where the method according to the invention is being carried out, the spectrum obtained for each product sample is contrasted against the model spectrum. To this end, the Euclidian distance between the intensity at each wavelength and the corresponding intensity for the model is calculated, with the weighting factor at each wavelength being applied. The weighting factors which are used were found in the modeling. The result is used to calculate the Euclidian distance of the sample. This is given as a reference quantity in terms of model standard deviations of the model.

The value of the Euclidian distance of the sample is subsequently compared with a fixed limit value. The limit value is derived from the mean Euclidian distance of the model and a probability range.

The mathematical method described above makes it possible to verify the composition of solutions and dispersions. If the composition of dispersions is being verified, then, in a particularly preferred embodiment of the invention, those weighting factors which were found on the basis of a solution are used in the determination step. The solution, on the basis of which the weighting factors are found, in this case preferably contains the same substance to be determined as the dispersion. In the dispersion, the substance may be dispersed as well as dissolved or—more generally—distributed between the continuous and disperse phases.

For example, insulin suspensions contain a proportion of dissolved insulin and a proportion of insulin suspended in crystalline form. This proportion of crystalline insulin may vary in wide ranges even if the insulin content is constant. In this case, it may prove advantageous for the weighting factors which were found on the basis of a pure insulin solution to be used in the determination step. Using the weighting factors of the pure solution eliminates the influence of scattering effects which are caused by the suspended crystals.

With the described mathematical evaluation method, evaluation of the product can be carried out at a high speed, for example within a time window of only 5 ms. This makes it possible to analyze a large number of products within a short time. The method is furthermore noninvasive and can function without contact. For example, it is therefore very suitable for the analysis of products on a packaging line or in conjunction with a filling system for cartridges or bottles. The analysis may be carried out in realtime and include 100% of the products being transported on the packaging line. At least 3, preferably at least 8 or even 50 or more products can be successively analyzed per second by the method according to the invention. For example, it is therefore suitable for the line control of product units in the production, filling and/or packaging of solutions or dispersions for pharmaceutical purposes.

With the method according to the invention, for example, it is possible to upgrade from spot-check control to 100% control when filling solutions or dispersions for pharmaceutical purposes.

The present invention also relates to an apparatus for determining the quantitative content of at least one substance in a moving product, which comprises a solution or dispersion in a container, comprising a radiation source, which emits radiation in the near infrared range, for irradiating the product;

a radiation reception device, which receives the radiation reflected by or transmitted through the product;

a spectrometer for receiving the radiation from the radiation reception device and for providing an output signal corresponding to the intensity of the radiation received at a number of different wavelengths;

a device for quantitatively determining the content of at least one substance contained in the dispersion or solution on the basis of the output signal.

The radiation reception device may have a converging lens and an optical fiber. The radiation reception device may have a photodiode array as its detector.

The apparatus preferably also has a calibration device, with which the quantitative content of the at least one substance can be determined by an alternative method, for example a high pressure liquid chromatograph.

The apparatus may furthermore have a sorting device used to reject those products not complying with specification which have been found by the method according to the invention. Products not complying with specification are those which do not lie within the predetermined integrity criteria.

If the apparatus is (also) used for the quantitative analysis of dispersions, then it preferably also comprises a device for homogenizing the dispersions to be quantified, before the dispersions are analyzed. The dispersions may, for example, be homogenized in the containers by a shaking mechanism or by a rotation mechanism. Homogenization may, however, also be achieved directly by the filling process.

The apparatus may furthermore have a device for detecting the product position, for example an imaging system or a photoelectric barrier.

The apparatus may be used in conjunction with a filling device, in which primary packaging is filled with the solutions or dispersions. The apparatus may also be a component of such a filling device.

In one embodiment of the invention, an apparatus which operates in transmission is provided, the device having an optical fiber which delivers the radiation emitted by the radiation source to the location of the product.

BRIEF DESCRIPTION OF THE DRAWINGS

FIG. 6 shows that the results using the method of the present invention (black rectangles) agree well with the results via the conventional method (HPLC, black crosses).

DETAILED DESCRIPTION OF THE INVENTION

The invention will be explained in more detail below with reference to the figures.

Figure 1:
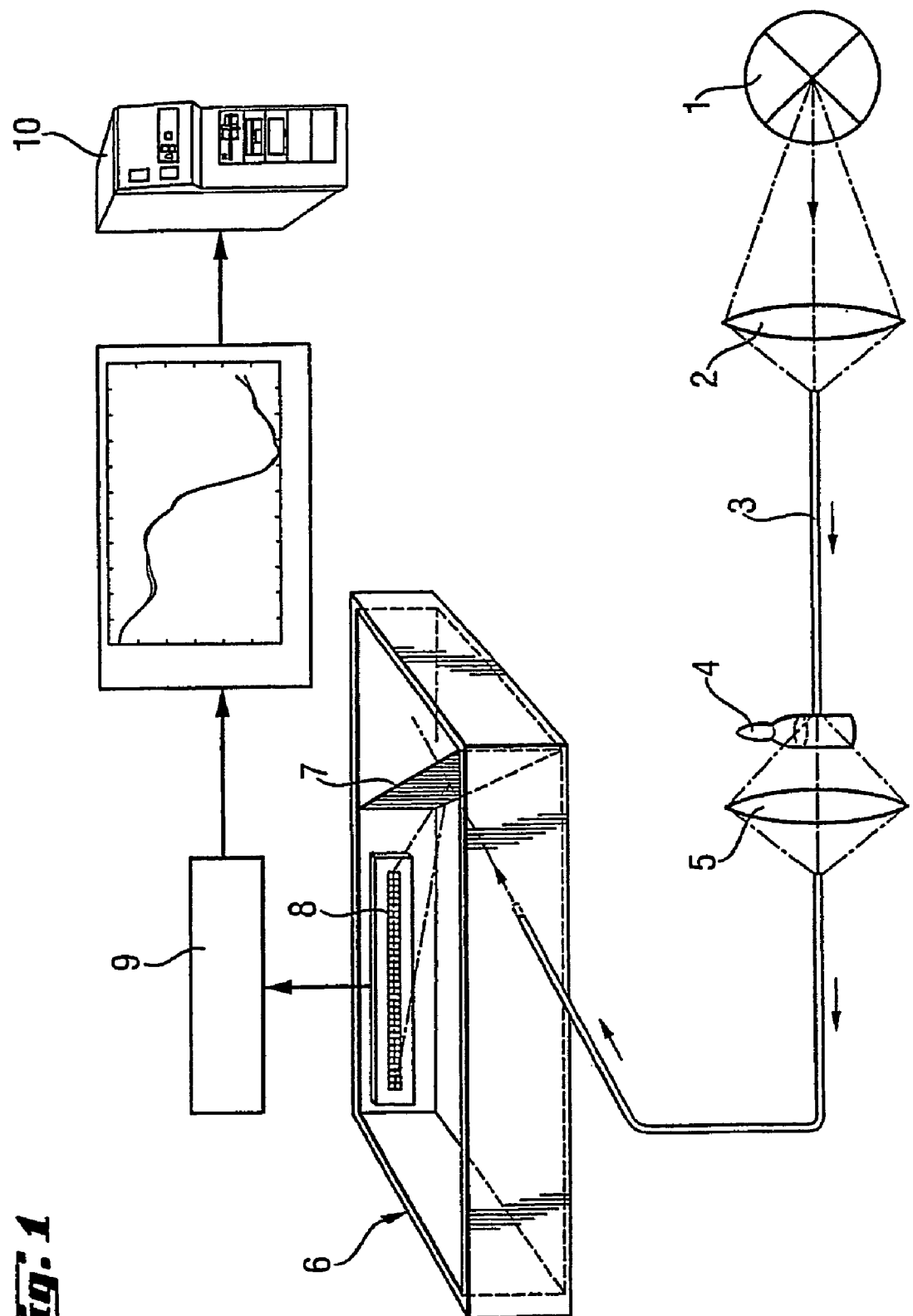
FIG. 1 schematically shows a device according to the invention, which operates in transmission.

FIG. 1 schematically shows a device according to the invention, which operates in transmission. The device comprises a radiation source (1), for example a tungsten halogen lamp. The near infrared radiation emitted by the radiation source is collimated by a converging lens (2) and delivered to the location of the product (4) by means of an optical fiber (3). The product may, for example, be a glass cartridge which contains an insulin suspension and, coming for example from a filling device, is transported past the end of the optical fiber (3) on a conveyor belt. The radiation transmitted by the product (4) is collimated by a converging lens (5) and delivered to the spectrometer (6) by means of an optical fiber. In the spectrometer (6), the transmitted radiation which contains the spectral information of the product (4) irradiated in transmission, is split into radiation of different wavelengths by means of a grating (7) and detected by a photodiode array (8). The intensities detected by the photodiode array as a function of wavelength are converted into digital signals by means of an A/D converter (9) and evaluated in the determination device (10), for example a PC.

EXAMPLE 1

The purpose of line-monitoring the insulin filling is quantitative control of the insulin content in 100% of the filled insulin vials. The insulin content of the filled insulin suspensions should in this case only deviate from the nominal value by at most +/−5%. Anomalies should be impeccably detectable.

In order to simulate monitoring of the insulin filling, calibrations were carried out with a set of calibration samples, which contained crystalline Insuman Basal® insulin in primary packaging (glass cartridges), and production samples were subsequently studied. Insulin packages with exactly known insulin contents of from 90 to 120% of the setpoint content were used for the calibration. The reference values were determined by HPLC. The cartridges were thoroughly shaken before the measurements, so that there was a homogeneous suspension.

The insulin spectra were recorded in transmission with a photodiode array spectrometer (MCS 511 NIR 1.7). The wavelength range of the measurement was from 960 to 1760 nm, the wavelength range of from 960 to 1360 nm being evaluated. A 20 W halogen lamp was used as the NIR radiation source. The spectrometer was regularly compared against reference standards. A BG5 filter and a BG9 filter were used for reference.

In order to preprocess the spectra, they were smoothed and normalized. The spectra were used in $0^{th}$ derivative. The scattering properties of the insulin samples were thereby kept in the spectra.

The spectra were subsequently evaluated by means of a multivariate evaluation method. A PLS (partial least squares) regression was used as the regression method, although it is also possible to use other multivariate evaluation methods. A mathematical relationship between the spectral information of the insulin samples and the insulin content is obtained from the regression. From the spectrum of an unknown sample, the insulin content of this sample can later be calculated with the aid of this relationship.

Figure 2:
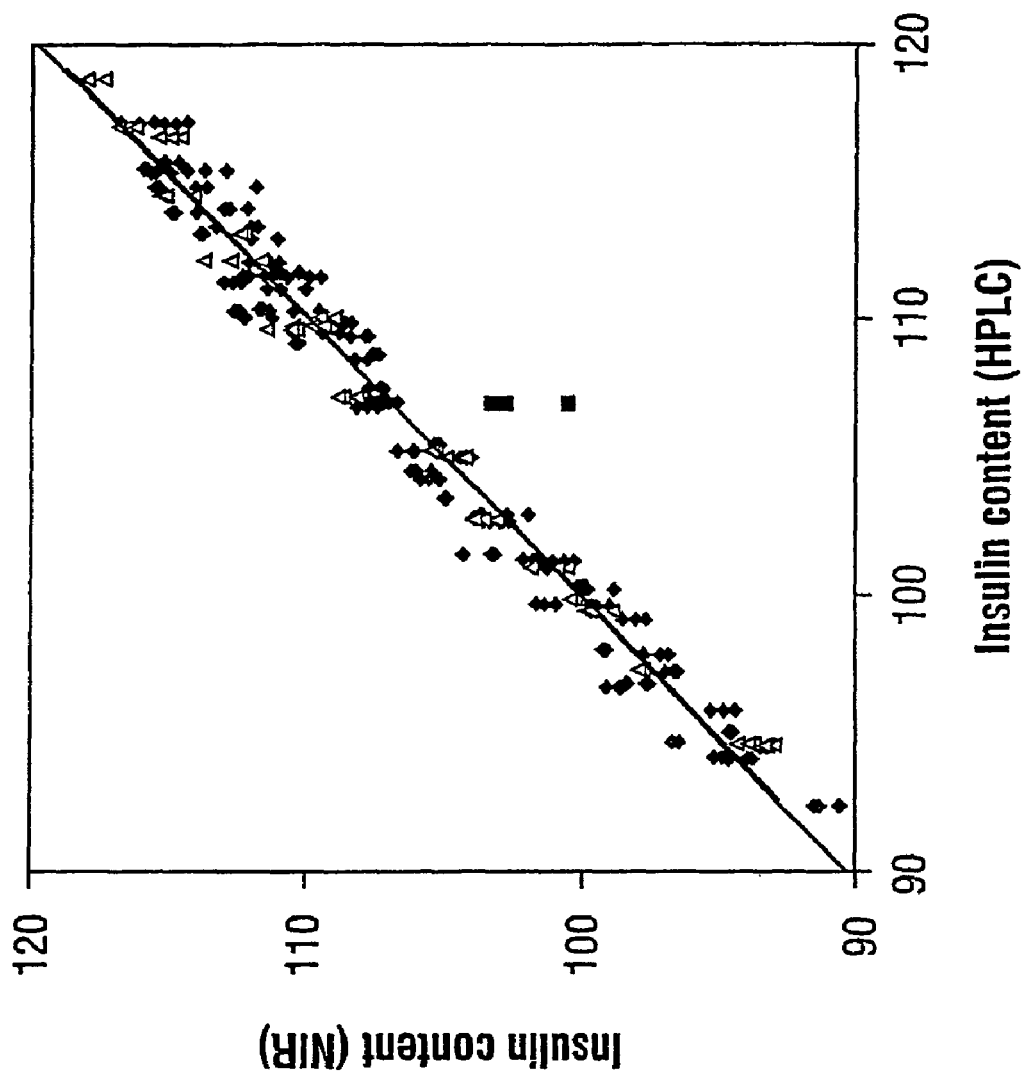
FIG. 2 shows the correlation between the values measured by HPLC and the values found from the NIR transmission spectra for the total insulin content of the Basal® insulin calibration samples (respectively in % of the setpoint content).

FIG. 2 shows the correlation between the values measured by HPLC and the values found from the NIR transmission spectra for the total insulin content of the Basal® insulin calibration samples (respectively in % of the setpoint content). It is clear that there is a good correlation between the values found from the NIR spectra and the values found by means of HPLC.

Process samples from the insulin production process were then studied. These are samples which were obtained in the regular production process and had been discarded as unfit for use. The total insulin content was found from the obtained NIR spectra with the aid of the multivariate regression equation. The same vials were subsequently studied by means of HPLC.

Figure 3:
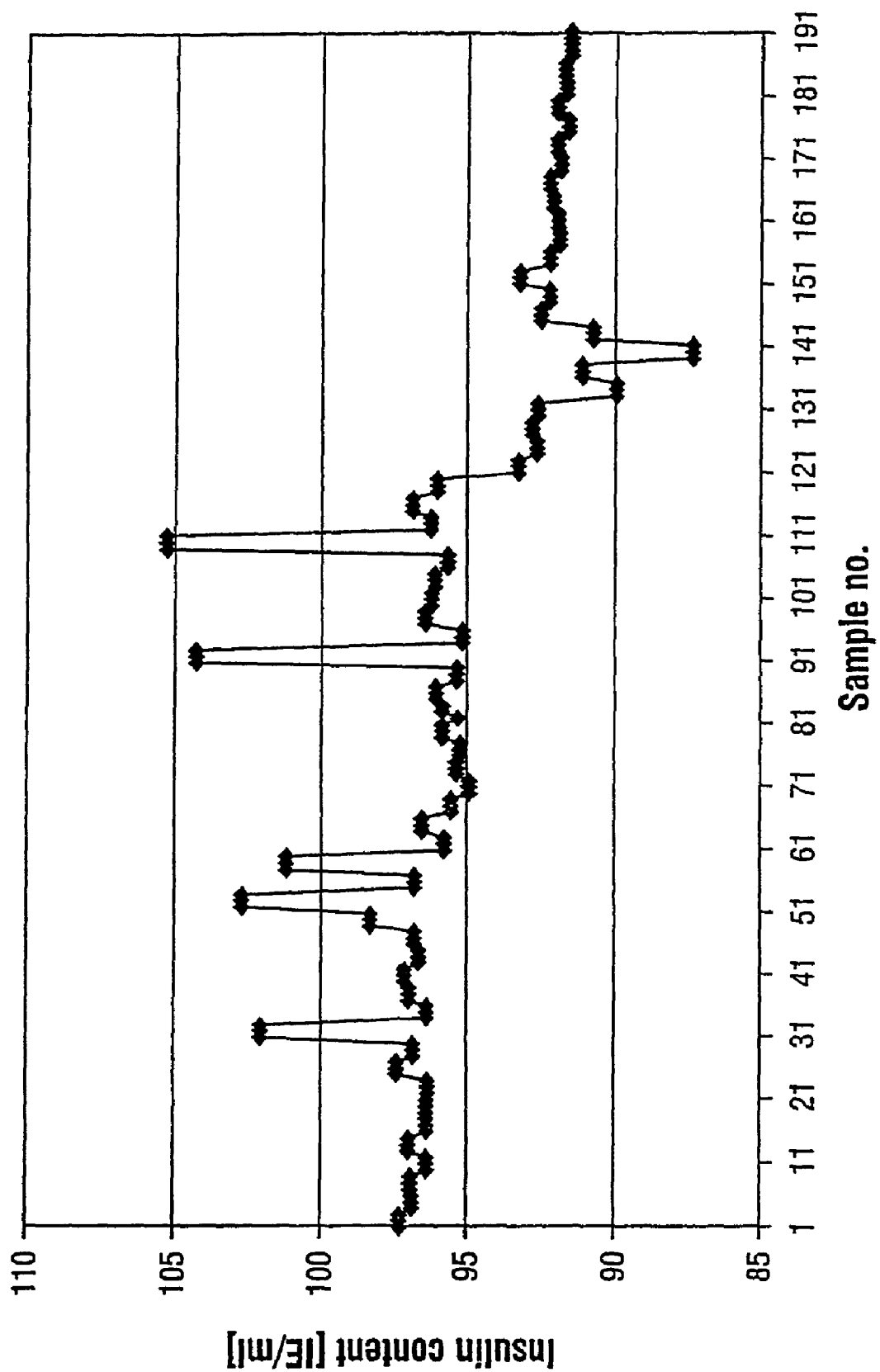
FIG. 3 shows the total insulin content of the studied samples as determined by HPLC.
Figure 4:
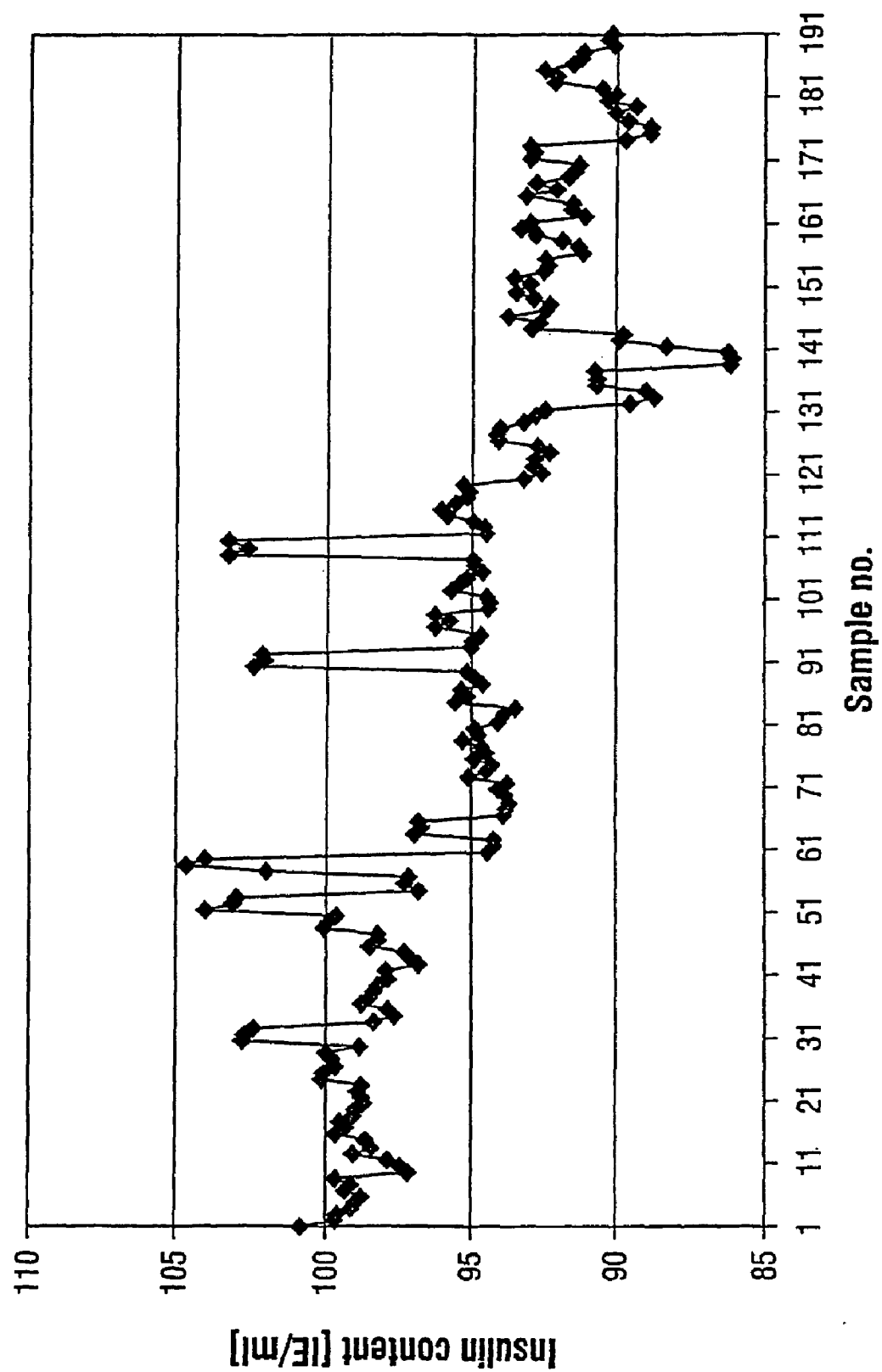
FIG. 4 shows total insulin content from the NIR spectra in the description as determined by the evaluation method described (both in IU).

FIG. 3 shows the total insulin content of the studied samples as determined by HPLC, and FIG. 4 shows their total insulin content from the NIR spectra in the description as determined by the evaluation method described (both in IU).

The values found from the NIR transmission spectra and the values found by HPLC show a good match. It is clear that the anomalies found by means of HPLC can be unequivocally detected with the aid of the smoothed and normalized NIR transmission spectra.

EXAMPLE 2

The purpose of line-monitoring the insulin filling is quantitative control of the insulin content in 100% of the filled insulin vials. The insulin content of the filled insulin suspensions should in this case only deviate from the nominal value by at most +/−5%. Anomalies should be impeccably detected. The monitoring should take place either during the filling, on moving insulin cartridges, or after the filling, on already filled cartridges. In either case, the measurement takes place through the primary packaging (glass cartridge) and in the moving contents.

To simulate the speeds involved in filling insulin cartridges, an optical control machine of the 288 type from EISAI Machinery was used. This machine can be equipped with insulin cartridges (suspensions) and causes the cartridges to rotate, so that a homogeneous suspension is formed by means of the metal balls in the cartridges. The NIR measuring apparatus constructed similarly to FIG. 1 was installed in this machine. The measurement took place in the moving, rotating cartridge at a rate of 150 cartridges per minute. Care must be taken to ensure that a homogeneous suspension is present at the time of measurement. The installed measuring apparatus consists of a 50 watt halogen lamp (Comar 12LL50), a holder for the lamp with integrated converging lens (for example Comar 20LH00), which focuses the focus of the radiation on the midpoint of the insulin cartridge, a second converging lens (for example Comar 80TC50), which collimates the transmitted radiation and transmits it via a coupling (for example Zeiss, No. 772571-9020-000) and an optical fiber (for example Zeiss, CZ-#1050-724) to a photodiode array detector (Zeiss, MMS NIR No. 301261). The analog signals at the detector are digitized and read out into a text file. In total, the radiation is measured at 128 photodiodes over a range from about 900 to 1670 nm. The time of measurement was triggered via a light barrier (Wenglor UM55PA2 & 083-101-202) which has caused a spectrum to be recorded as the cartridge passes through the optical path. The PDA detector was initially compared against Spectralon at the day of each measurement.

The apparatus described was used to measure insulin preparations (suspensions) of the type Insuman Basal, Insuman Comb 25 and Insuman Comb 50. Each spectrum took 8 milliseconds [ms] to record.

The insulin spectra were judged against model spectra using the method described in the description part. The model spectra and their variability were obtained by measuring eight water-filled cartridges. The model and insulin spectra were smoothed and autoscaled. The Euclidian distance of each insulin spectrum from the mean model spectrum was subsequently computed using wavelength-specific weighting factors.

Figure 5:
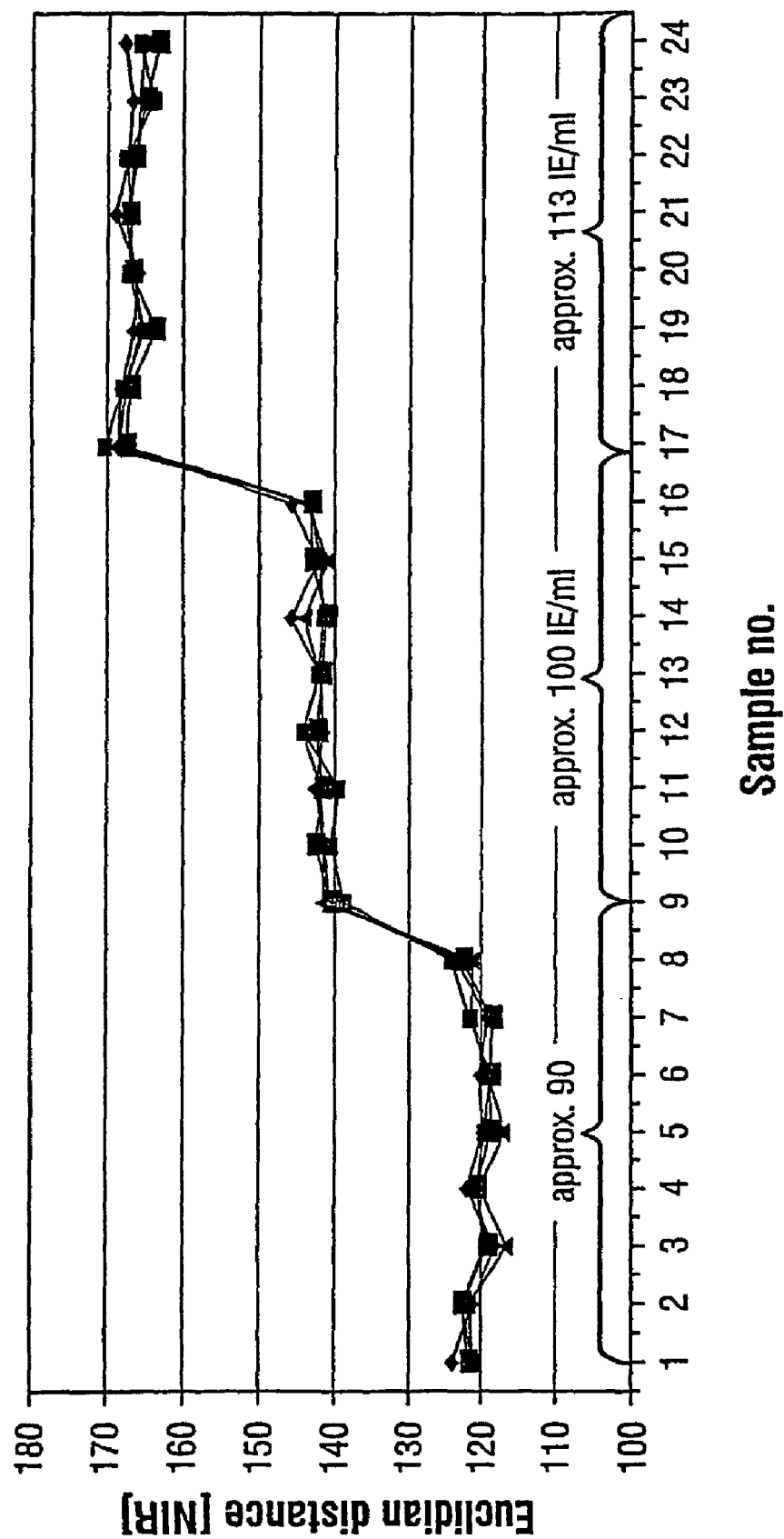
FIG. 5 shows the dependence of the insulin content on Euclidian distance.

Samples of differing concentration were prepared and the Euclidian distances from the model spectrum computed for each of the Insuman Basal, Insuman Comb 25 and Insuman Comb 50 preparations. The dependence of the insulin content on the Euclidian distance is shown in FIG. 5 for Insuman Comb 25 as an example of the different types of preparations. The precision of the method is likewise illustrated, since 4 repeat measurements are depicted. A calibration function ($2^{nd}$ degree polynomial) results for each type of preparation whereby the Euclidian distance can be converted into insulin contents. After conversion of the Euclidian distance into insulin contents, two correction factors have to be taken into account. The insulin content has to be corrected for the temperature of the measured material. In addition, a preparation-specific factor has to be applied to reflect the different crystal size distributions in the suspension. As a result, the content can either be expressed as a percentage in relation to the first 20 results. In that case, the content is obtained in percent of the target value, based on the first cartridges of a filling. On the other hand, the insulin content found can also be corrected by a factor which results from the ratio of the uncorrected value of a sample to the concurrently measured insulin content. In FIG. 6, this correction factor has been determined for sample 16 and a series of cartridges of unknown content have been evaluated for Insuman Comb 25 by way of example for other types of preparations. The samples in question had been obtained in the regular production process and had been discarded as unfit for use. The correction factor for the temperature was not applied, since there were no differences in the course of the measurement. Further samples were analyzed by HPLC in spot-check fashion. It can be seen that the results using the method of the present invention (black rectangles) agree well with the results via the conventional method (HPLC, black crosses). It is unambiguously and precisely possible to judge whether a value is within the limits of 95 to 105% or outside.

The invention claimed is:

1. A method for quantifying the composition of a moving packaged product containing a dispersion comprising:
    irradiating the packaged product with a radiation source in the near infrared range;
    receiving radiation which is reflected by or transmitted through the packaged product, and providing an output signal corresponding to the intensity of the radiation received at a number of different wavelengths; and
    determining, using factors which are found on the basis of a solution, whether or not the packaged product lies within predetermined integrity criteria on the basis of the output signal using a mathematical method,
wherein
    the moving packaged product comprises a container transparent for NIR radiation containing a solution or homogeneous dispersion,
    the content of at least one substance contained in the dispersion or solution is quantitatively determined on the basis of the output signal, and
    said substance contained in the dispersion is distributed between the continuous and disperse phases.

2. The method as claimed in claim 1, wherein the product contains a dispersion which contains crystalline and/or dissolved insulin.

3. The method as claimed in claim 1, wherein the moving product is a solution or dispersion in primary packaging.

4. The method as claimed in claim 1, wherein the moving product is an insulin vial or insulin cartridge.

5. A method for quantifying the composition of a moving packaged product containing a dispersion comprising:
    irradiating the packaged product with a radiation source in the near infrared range;
    receiving radiation which is reflected by or transmitted through the packaged product, and providing an output signal corresponding to the intensity of the radiation received at a number of different wavelengths; and
    determining, using weighting factors which are found on the basis of a solution, whether or not the packaged product lies within predetermined integrity criteria on the basis of the output signal using a mathematical method,
wherein
    the moving packaged product comprises a container transparent for NIR radiation containing a solution or homogeneous dispersion,
    the content of at least one substance contained in the dispersion or solution is quantitatively determined on the basis of the output signal,
    the solution for finding the weighting factors and the dispersion contain the same substance to be quantitatively determined, and
    said substance contained in the dispersion is distributed between the continuous and disperse phases.

6. The method as claimed in claim 5, wherein the product contains a dispersion which contains crystalline and/or dissolved insulin.

7. The method as claimed in claim 5, wherein the moving product is a solution or dispersion in primary packaging.

8. The method as claimed in claim 5, wherein the moving product is an insulin vial or insulin cartridge.

* * * * *

UNITED STATES PATENT AND TRADEMARK OFFICE
CERTIFICATE OF CORRECTION

| | | |
|---|---|---|
| PATENT NO. | : 7,755,051 B2 | Page 1 of 1 |
| APPLICATION NO. | : 11/762968 | |
| DATED | : July 13, 2010 | |
| INVENTOR(S) | : Christian-Peter Christiansen et al. | |

It is certified that error appears in the above-identified patent and that said Letters Patent is hereby corrected as shown below:

In column 10, line 5, in claim 1, delete "using factors" and insert -- using weighting factors --, therefor.

In column 10, line 19, in claim 2, after "which contains" insert -- at least one insulin selected from the group consisting of --.

In column 10, line 19, in claim 2, delete "and/or" and insert -- and --, therefor.

In column 10, line 21, in claim 3, after "moving" insert -- packaged --.

In column 10, line 23, in claim 4, after "moving" insert -- packaged --.

Signed and Sealed this
Fifth Day of April, 2011

David J. Kappos
*Director of the United States Patent and Trademark Office*